(12) United States Patent
Trösch

(10) Patent No.: US 7,374,928 B2
(45) Date of Patent: May 20, 2008

(54) BIO-REACTOR FOR THE CULTIVATION OF MICRO-ORGANISMS AND METHOD FOR THE PRODUCTION THEREOF

(75) Inventor: Walter Trösch, Stuttgart (DE)

(73) Assignee: Fraunhofer-Gesellschaft zur Forderung der angewandten Forschung e.V, Munich (DE)

( * ) Notice: Subject to any disclaimer, the term of this patent is extended or adjusted under 35 U.S.C. 154(b) by 670 days.

(21) Appl. No.: 10/381,812

(22) PCT Filed: Sep. 24, 2001

(86) PCT No.: PCT/EP01/11022

§ 371 (c)(1),
(2), (4) Date: Oct. 16, 2003

(87) PCT Pub. No.: WO02/31102

PCT Pub. Date: Apr. 18, 2002

(65) Prior Publication Data

US 2004/0048364 A1    Mar. 11, 2004

(30) Foreign Application Priority Data

Oct. 6, 2000 (DE) .................... 100 49 437

(51) Int. Cl.
*C12M 1/00* (2006.01)
*C12M 3/00* (2006.01)
*C12M 1/14* (2006.01)
*C12M 1/10* (2006.01)
*C12M 1/36* (2006.01)

(52) U.S. Cl. .............. 435/292.1; 435/292.1; 435/294.1; 435/287.8; 435/288.2; 435/295.2; 435/299.2; 435/299.1; 435/288.1

(58) Field of Classification Search ............. 435/292.1, 435/294.1, 287.8, 288.1, 288.2, 295.2, 299.2, 435/299.1
See application file for complete search history.

(56) References Cited

U.S. PATENT DOCUMENTS

| | | | | |
|---|---|---|---|---|
| 3,594,277 A | * | 7/1971 | Mako | 435/71.1 |
| 3,955,317 A | | 5/1976 | Gudin | |
| 3,959,923 A | * | 6/1976 | Selke | 47/1.4 |
| 4,654,308 A | * | 3/1987 | Safi et al. | 435/294.1 |
| 5,534,417 A | * | 7/1996 | Arad et al. | 435/67 |
| 5,772,887 A | * | 6/1998 | Noah et al. | 210/617 |
| 6,509,188 B1 | * | 1/2003 | Trosch et al. | 435/292.1 |

FOREIGN PATENT DOCUMENTS

| | | |
|---|---|---|
| DE | 23 58 701 | 6/1975 |
| DE | 41 34 813 A1 | 4/1993 |

(Continued)

*Primary Examiner*—Gladys J P Corcoran
*Assistant Examiner*—Nathan A. Bowers
(74) *Attorney, Agent, or Firm*—Dickstein Shapiro LLP

(57) ABSTRACT

The invention relates to a bioreactor for cultivating microorganisms, as well as a method for its production. The invention is characterized in that the bioreactor (1) comprises two identically constructed base elements (2,3) that are constructed in trough shape and consist of a bottom part (4) and four side parts (5) arranged on a bottom part (4) and having an inside depth $T_1$. The base element (2,3) consists of a light permeable material. The identically constructed base elements (2,3) are arranged on each other so as to exactly cover each other. A flow guide device is arranged inside the identically constructed base elements (2,3).

28 Claims, 3 Drawing Sheets

FOREIGN PATENT DOCUMENTS

| | | |
|---|---|---|
| DE | 42 13 015 A1 | 10/1993 |
| EP | 0 738 686 A1 | 4/1996 |
| FR | 1307047 | 10/1962 |
| FR | 2588271 | 4/1987 |
| GB | 291146 | 5/1928 |
| GB | 2235210 | 2/1991 |
| JP | 5-245496 A | 9/1993 |

* cited by examiner

BIO-REACTOR FOR THE CULTIVATION OF MICRO-ORGANISMS AND METHOD FOR THE PRODUCTION THEREOF

FIELD OF THE INVENTION

The invention relates to a bioreactor for cultivating microorganisms. It furthermore relates to a method for producing such a bioreactor.

BACKGROUND OF THE INVENTION

Bioreactors are fermenters in which biological conversions of substances are performed with enzymes, microorganisms (bacteria, fungi, yeast, algae) as well as animal and plant cells. It should be possible to create optimum conditions, specific to each process, with respect to temperature, pH value, and nutrient concentration in the bioreactor. The tasks of a bioreactor therefore include mass transfer within the fluid phase (mixing), dispersion in a second phase—in most cases air—in order to obtain a large phase boundary surface for good mass transfer (separation), and thermal transfer for dissipating the generated heat. The design of a bioreactor depends on its applications and therefore must take into account the specific requirements of the biological system used.

In order to cultivate phototrophic microorganisms, so-called photobioreactors are used. Among potential designs, the airlift photobioreactor is considered to be especially suitable for cultivating phototrophic microorganisms and growing them to a high cell density. The airlift photobioreactor often has a column-shaped reactor vessel, in which introduction of air creates a fluid circulation within a loop established by the construction. The airlift bioreactor is divided thus into a gassed and ungassed zone, which are interconnected at the bottom and top so that the hydrostatic pressure differential causes a pump effect that results in an outflow of fluid in the gassed zone. As the mixing of the reactor medium is due exclusively to the aeration, this photobioreactor design enables good mixing and a high gas-fluid mass exchange with low energy consumption. Such an airlift photobioreactor is described, for example, in DE 199 16 597.

As cultivation of phototrophic microorganisms requires high-intensity incident light radiation, especially deep in the reactor, photobioreactors preferably have a large surface-to-volume ratio and thus require a relatively high expenditure of material. Because of the materials used, such as glass or Plexiglas, the production of such a photobioreactor is relatively complicated, material- and cost-intensive.

BRIEF SUMMARY OF THE INVENTION

The invention is therefore based on the objective of creating a cost-efficient bioreactor for cultivating phototrophic organisms, especially microorganisms, which can be produced simply, quickly, cost-efficiently, and reliably. In addition, a suitable method for its production should be described. Furthermore, a cost-efficient method for cultivating microorganisms should be described.

This objective is realized with a bioreactor described herein. The bioreactor according to the invention has a housing made from a light-permeable material. The housing preferably is constructed with a greater length than width and, for example, gas bubbles flow through it, preferably in longitudinal direction. The gas bubbles, preferably air bubbles, are generated by introducing gas into a fluid located inside the bioreactor. A flow guide device comprising at least two septa arranged transversely to the flow direction is located inside the housing. Within the context of the invention, the term "septa" means superficial structures that separate the housing into interconnected compartments. The function of the septa is to guide the flow through the housing of the bioreactor following a specific flow path.

The septa are preferably designed and positioned in the housing in such a way that an essentially meander-shaped flow path for the gas bubbles is obtained inside the housing. The moving gas bubbles cause the fluid between two consecutive septa to perform a revolving movement. The arrangement of the septa has the result that the rotating direction of the revolving movement is inverted from compartment to compartment. This creates a turbulent flow and good mixing of the organisms contained inside the bioreactor.

It is advantageous that the septa are constructed and arranged in the housing in such a way that they limit the flow cross-section in each case to only a gap. The gaps defined by the septa are arranged so as to alternate on opposing side walls of the housing. During operation, the bioreactor contains a fluid into which the gas is introduced. When flowing through the gap, the gas bubbles generated as a result of the gas introduction result in a revolving flow in the compartments formed by the gaps in the housing.

The septa preferably are interconnected by at least one support element. As a result of the support element, the septa are fixed in their position relative to each other and in the housing. The support element, for example, may be a narrow bridge that extends in the flow direction and practically does not influence the flow in the housing. The septa also may be attached to the housing or be molded in one piece with the housing.

The housing preferably comprises two, in particular identically constructed, base elements, each of which has an inside depth $T_3$ corresponding to half of the inside depth T of the bioreactor, whereby the base element is constructed trough-like from a bottom part and four side parts arranged on the bottom part and having an inside depth $T_1$. The base element consists of a light-permeable material, and the identically constructed base elements are arranged on each other so as to exactly cover each other. The flow guide device is arranged inside the identically constructed base elements. The bioreactor according to the invention can be constructed in a simple manner quickly, cost-efficiently, and reliably, which is due, among other things, to these characteristics, especially due to its design as two identically constructed base elements. The flow guide device may be a separate component. However, the flow guide device also may be constructed in one piece with the base elements.

BRIEF DESCRIPTION OF THE DRAWINGS

The following figures illustrate the invention using different embodiments.

DETAILED DESCRIPTION OF THE INVENTION

Figure 1:
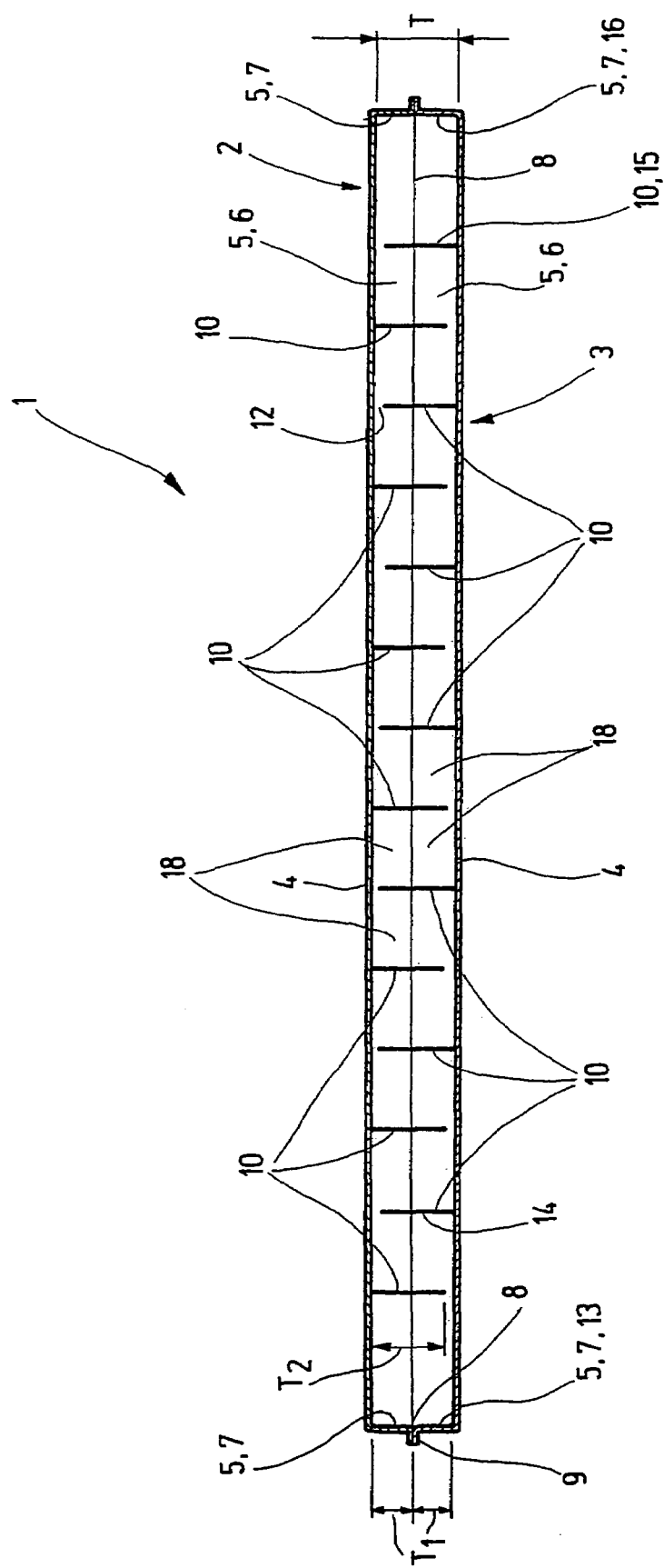
FIG. 1 shows a side view in form of a section of the bioreactor.
Figure 2:
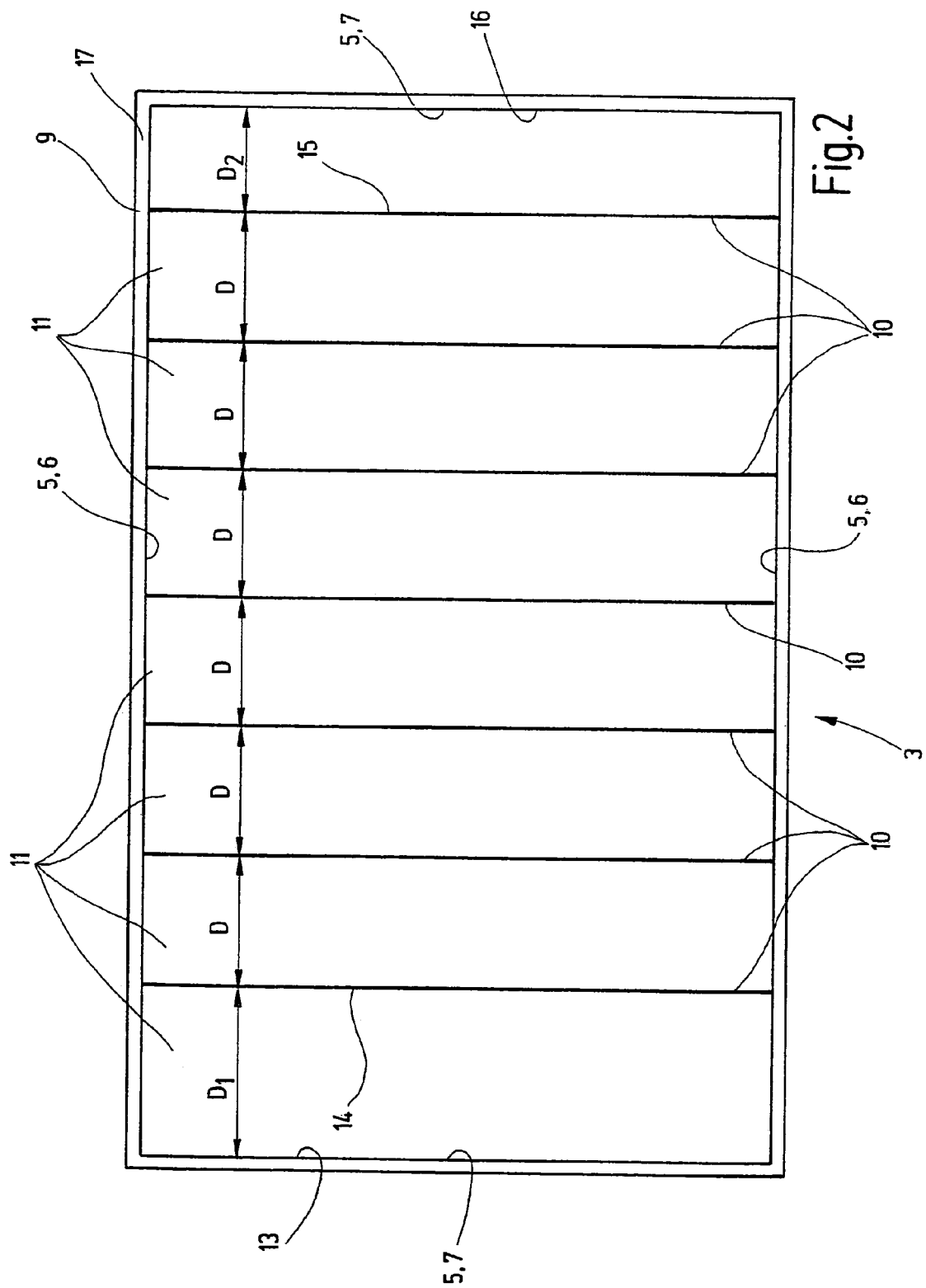
FIG. 2 shows a top view of the bottom base element of the bioreactor.

A special embodiment of the invention is characterized in that the flow guide device comprises at least one septum, preferably several septa, through which two side parts, called longitudinal side parts, which are arranged parallel, opposite from each other at a right angle to the septum or septa, are interconnected in such a way that in the trough-like base element several chambers that are open on the side facing away from the associated bottom part are formed, whereby the at least one septum has a septum depth $T_2$ that is smaller than or equal to the inside depth T of the reactor and greater than half of the inside depth T of the reactor, whereby the distances D between the individual septa are equal and the distance $D_1$ between a side part called the first transverse side part and a consecutive septum or the immediately adjoining septum of this base element do not equal the distance $D_2$ between a side part called the second transverse side part and a consecutive septum or the immediately adjoining septum of this base element or an integer multiple of it, whereby the identically constructed base elements with their chamber openings are arranged opposite each other in such a way on top of each other that the distance $D_2$ overlaps the first distance $D_1$. The production of the bioreactor according to the invention is substantially simplified by integrating the flow guide device into the base elements.

It is preferably provided that the two identically constructed base elements are placed on top of each other in opposite orientation and are glued, welded, or in another manner connected to each other. The special geometry of the septa, and in particular of their distances relative to each other and to the transverse side parts, cause the reactor space formed by the two base elements to be divided into a plurality of different compartments that are in part separated from each other by the septa, and whereby the septa are formed alternately, when seen from the longitudinal axis of the formed reactor, by one or the other base element. The septa of the two base elements alternatingly form—starting once from one bottom part, for example from the top, and starting from the other bottom part, for example from the bottom—compartments through which the reactor medium is able to flow. It is preferably provided that the septa's inside depth $T_2$ is smaller, preferably somewhat smaller than or identical to the inside depth T of the reactor. This means that in the last mentioned embodiment, the septa completely close off the compartments from each other. As a result of the flexible material structure, the flow is however able to bend the septa sideways, enabling a fluid flow from the reactor inlet through the compartments to the reactor outlet. In another embodiment, the inside depth $T_2$ of the septa is smaller than the inside depth T of the reactor, so that a gap remains through which the fluid is also able to flow while forming turbulences.

According to the invention, the term "trough-like" means a base element defined by five rectangles, which is formed from a bottom part and four side parts, and wherein the area opposite from the bottom part remains open, i.e. is not covered by a second bottom part. The corners of the base element hereby can be constructed either angular or rounded.

The septa of a base element are constructed with respect to their inside depth $T_2$ so that they just touch either the bottom part of the opposing base element in the bioreactor according to the invention or form a gap between septum top edge and bottom part so that a medium in the reactor is able to flow past this point on the septum while forming turbulences. It is provided that the inside depth $T_2$ of the septa is 60, 70, 80, 90, 95, 96, 97, 98, and preferably 99% of the inside depth T of the bioreactor. The inside depth $T_2$ of the septum or the inside depth $T_1$ of the side parts (corresponding to inside depth $T_3$ of the base elements) mean the depth of these components minus the material thickness of the bottom part.

The term "inside depth T" of the bioreactor means the depth of the bioreactor minus the material thickness of the two bottom parts of the base elements that constitute the bioreactor. By designing the bioreactor with septa arranged at a distance to each other and alternating on the bottom parts of the two opposing base elements, the reactor space of the bioreactor according to the invention is constructed as a so-called turbulent cell column. The septa hereby create a turbulent flow of the medium in the bioreactor in such a way that they substantially decrease the flow diameter and in this way act as a throttling point, resulting in an eddy formation and intensive mixing. The bioreactors according to the invention are therefore especially suitable for cultivating phototrophic organisms, such as microorganisms or plants, for example algae.

Another special embodiment of the invention is characterized in that the base element is provided in longitudinal direction with at least one reinforcement. The longitudinal direction, related to the base element, is defined by the arrangement of the longitudinal side parts. Correspondingly, the transverse direction is established by the arrangement of the transverse side parts of the base element. In transverse direction, the septa ensure a sufficient stability of the base element. The additional longitudinal reinforcement is ensured by a sufficient stability in the longitudinal direction of the base element also. This prevents an undesired deformation of the bioreactor during operation.

Another special embodiment of the invention is characterized in that the reinforcement is formed by several U-shaped bearing elements, which are individually connected with two adjoining septa and in between with the bottom part of the associated base elements, whereby the first and second transverse side part each are also connected via a U-shaped bearing element with the following septum. This achieves a reinforcement of the base element between the first and second transverse side part in a simple manner. The U-shaped bearing elements are constructed preferably in one piece with the associated base element. This simplifies the production of the bioreactor according to the invention. The U-shaped bearing elements furthermore have essentially the same thickness as the septa. As a result, the flow in longitudinal direction through the bioreactor according to the invention is not adversely affected. As an alternative to the individual bearing elements, a continuous bearing element extending between the two transverse side parts of a base element may be provided. Additionally or alternatively to the bearing elements, braces may be provided on the outside of the base element also. In addition, a matrix material, for example in the form of a fiber mat, may be integrated into the material of the base element in order to increase the stability of the base element.

Another special embodiment of the invention is characterized in that the wall thickness of the septa increases towards the bottom part of the associated base element. This increases the stability of the septa while it saves material at the same time. It also ensures a simple unmolding of the septa if the base element is produced, for example, by injection molding.

An advantageous embodiment of the bioreactor provides that the light-permeable material of which the base element consists or which is the major component of the base element is a flexible foil, preferably of plastic, such as, for example, polypropylene, polystyrene, or polyethylene. The use of such a reactor material provides substantial advantages with respect to cost when compared to previously used materials made from glass or Plexiglas. The use of a flexible foil is possible in particular because of the previously mentioned geometrical characteristics of the base element. The reactor space consisting of the flexible foil therefore, on the one hand, resists the hydrostatic pressure that is generated, and, on the other hand, a high eddying or revolution formation in the flow of the reactor medium is ensured by gas introduction at the underside of the reactor, which is the prerequisite for achieving high photosynthesis activity.

To achieve appropriate stiffness, it is advantageous if the wall thickness of the side parts of the base element in a preferred embodiment is greater than the wall thickness of the septa of the base element.

In an another advantageous embodiment of the bioreactor, both of its base elements are provided on the edges of the side parts that are at a distance to the bottom part with an edge or collar projecting essentially at a right angle outward. This results in a secured and defined contact, at which both of the base elements can be connected to each other, for example by gluing or ultrasound. An increased contact surface furthermore increases the flexural strength of the bioreactor.

According to one further development of the bioreactor, it is provided that the reactor space formed by both base elements has a surface enlargement greater than a straight-surfaced enveloping surface of its volume. Such a surface enlargement is already realized with the presence of the septa. It is furthermore possible to construct the reactor surface in meander or sinus shape. It would also be possible, however, that the envelope of the bioreactor has extensions or convexities in order to enlarge the surface. The surface enlargement provides a better spatial distribution of the light over the reactor cross-section, and thus an optimization of the light intensity in the entire reactor. The surface enlargement measures also have a turbulence-increasing effect on the flow configuration of the reactor medium. As already mentioned above, a turbulent flow configuration with formation of eddies or revolutions should be desired, as this makes it possible to increase the amount of incident light and thus the photosynthesis activity. To achieve maximum photosynthesis activity, an incident light radiation frequency of at least 1 Hertz must be enabled (flashing light effect).

In another advantageous embodiment of the bioreactor, it has elements that guide light from the outside into the reactor space in order to increase the energy density in the reactor space. This is accomplished, for example, with so-called wavelength shifters. The light portion not absorbable by phototrophic microorganisms is converted by wavelength shifters in such a manner that the greatest possible light portion or the entire of the radiation can be shifted to the frequency band that can be absorbed by the photocenter of the employed phototrophic microorganism. This increases the holometric radiation density specifically in such a way that the productivity per reactor volume is significantly increased compared to bioreactors irradiated with normal light. A wavelength shift can be achieved, for example, in that a wavelength-shifting substance is applied as a coating to the inside or outside of the reactor wall. A wavelength shift is also possible with rods, plates, fibers, or particles in the reactor space.

It is advantageously provided that the bioreactor has connections and connecting lines for supplying/removing gases and/or fluids. This makes it possible to exchange operating materials fully automatically using a control unit. It is furthermore provided that the connecting lines can be cooled and/or heated. This advantageously makes it possible to maintain both the added as well as the removed substances at a defined temperature. Cooling or heating can be achieved via internal or external loops. Such cooling or heating again can be monitored and regulated using the monitoring or control unit. The bioreactor according to the invention preferably is positioned so that the longitudinal side parts of the base elements forming the bioreactor are arranged vertically. In this arrangement of the bioreactor, one each transverse side part of the two base elements is oriented downward, and one transverse side part is oriented upward. Preferably, a gas inlet is provided in one of the two transverse side parts that are oriented downward. Through the gas inlet, gas can be introduced into the reactor medium. In the reactor medium, the gas forms bubbles that rise to the top. The gas consists of, for example, air that may be discharged at a gas outlet provided in one of the upward-oriented transverse side parts of the two base elements. The gas introduction into the bioreactor according to the invention causes a revolving, turbulent flow to form in the compartments of the bioreactor. The gas used for driving is preferably enriched with $CO_2$ in order to accelerate the growth of the microorganisms in the bioreactor. Growth can be limited by limiting incident light radiation into the bioreactor. The bioreactor according to the invention furthermore can be provided with fluid return lines extending from the top to the bottom. The fluid return lines are used to improve the mixing of the reactor medium. The fluid return lines also may extend outside the bioreactor and may be cooled.

According to a further development of the bioreactor, it is provided that the bioreactor is part of a system of several individual bioreactors that are arranged serially on the fluid side. Such a design allows an increased performance of the bioreactor. The invention therefore also relates to systems constructed from individual bioreactors according to the invention that are arranged serially and/or parallel to each other.

The objective is furthermore realized with a method for producing a bioreactor. In this method, a first step consists of producing a strand from a light-permeable material, said strand comprising a plurality of directly adjoining, serially arranged base elements, whereby the base elements are arranged behind each other in each case in orientation $D_2$ of one base element followed by orientation $D_1$ of another base element. This strand is preferably produced using an injection molding process. In a second step, the strand is divided into the individual base elements, and in a third step, two each of the consecutive base elements are arranged on top of each other so as to exactly cover each other and with the chamber openings facing each other by folding over a second base element onto a first base element, so that the distance $D_2$ overlaps a distance $D_1$. After this, or simultaneously, the two base elements are glued to each other or welded to each other via ultrasound at the respective outward-projecting edge of the side parts of the base element. The method makes it possible to produce a bioreactor simply and quickly. As the previously mentioned steps can be performed in a fully automated manner, a high degree of reliability is achieved in the production of the bioreactor.

The objective is furthermore realized with a method for cultivating microorganisms. The microorganisms are introduced into a fluid-filled bioreactor and are cultivated there under appropriate conditions. The cultivation preferably is performed with gas introduction. As a result of the gas introduction, gas bubbles that contribute to a good mixing of the microorganisms in the bioreactor form in the fluid. It is advantageous to perform the cultivation with an addition of $CO_2$. The added $CO_2$ accelerates the growth of microorganisms in the bioreactor. The cultivation is preferably performed with cooling. The cooling may be accomplished with external or internal cooling loops.

Other advantageous designs are derived from the secondary claims.

FIG. 1 shows a bioreactor 1 consisting of two identically constructed, rectangular base elements 2 and 3 of a thin, flexible, light-permeable plastic foil. Each of the two base elements 2 and 3 is constructed in one piece of a bottom part 4 and septa 10 arranged on the bottom part 4, as well as side parts 5 with an inside depth $T_1$ also arranged on the bottom part 4, whereby two each side parts 5 are constructed as longitudinal side parts 6, and two each as transverse side parts 7. The longitudinal side parts 6 arranged parallel and facing each other and the transverse side parts 7 arranged at a right angle to the former also parallel and facing each other have on their edge 8 that is at a distance to the bottom part 4 a collar 9 projecting outward at a right angle. The longitudinal side parts 6 of a base element 2 or 3 are interconnected by seven septa 10 of the same flexible, thin plastic foil in such a way that in base element 2 or 3 eight rectangular chambers 11 are formed, which are open towards the top or the bottom. Each of the septa 10 is arranged at the same distance at a distance D in longitudinal direction relative to each other. The distance between a first transverse side part 13 and a first subsequent septum 14 is called distance $D_1$, which is greater than the distance D between the individual septa 10. In contrast, the distance $D_2$ between the last septum 15 and the second transverse side part 16 is smaller than the distance D between the septa 10. The septa have the same inside depth $T_2$, which is smaller than double the inside depth $T_1$ of base element 2 or 3, but greater than the inside depth $T_1$ of a base element 2 or 3. In the assembled state of the two base elements forming the bioreactor 1, this results in a gap 12 between the top edges of the septa 10 of one base element 2 and the bottom part 4 of the opposing base element 3 or 2. The two identically constructed base elements 2 and 3 are arranged so as to exactly cover each other with their chamber openings 11 on opposing sides, i.e. in such a way that the distance $D_2$ of a base element 2 or 3 overlaps the first distance $D_1$ of the other base element 3 or 2, i.e. is arranged so as to be directly facing it. The two identically constructed base elements 2 and 3 are therefore arranged on top of each other in such a way that the upper base element 2 rests on the lower base element 3 in a folded-over position, i.e. rotated by 180° about its transverse axis. Both base elements 2 and 3 contact each other on contact surface 17 formed by the collar 8 of side parts 4 and are fluid-tight connected to each other there. Since in the assembled state, when seen over the longitudinal axis of the bioreactor, the septa 10 of one bottom part 4 of the base element 2 or 3 each are arranged alternatingly with the septa 10 of the opposing bottom part 4 of the base element 3 or 2, each of the formed gaps 12 is also arranged alternatingly on the bottom part 4 of one base element 2 or 3 and the bottom part 4 of the other base element 3 or 2. The septa 10 which have been arranged alternatingly in this manner therefore form compartments 18 in that a septum 10 of a base element 2 or 3 projects into chamber 11 of the opposing base element 3 or 2 and in this way divides this chamber 11 into two compartments 18. The medium inside the reactor is guided along the longitudinal axis of the bioreactor 1 in meander-shape around septa 10 through gaps 12 of bottom part 4 of base element 2 or 3 to bottom part 4 of the opposing base element 3 or 2. The base elements are produced using a deep-drawing or injection molding process.

Figure 3:
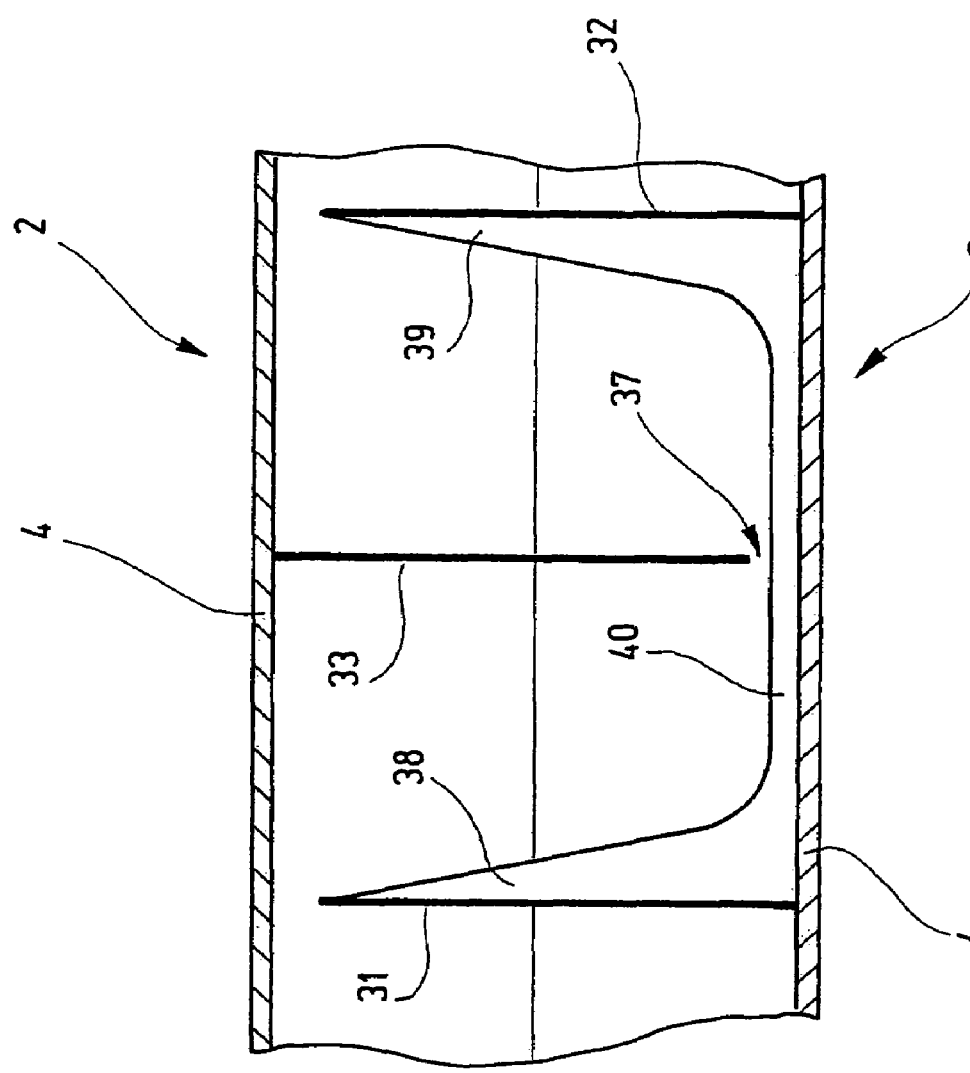
FIG. 3 shows an enlarged excerpt of FIG. 1 according to another embodiment of the invention with longitudinal reinforcement.

In the embodiment, of which an enlarged excerpt is shown in FIG. 3, two septa 31 and 32 associated with base element 3 are connected with each other via a bearing element. The bearing element has the shape of a U with two legs 38 and 39 that are connected via a bridge 40 with each other. Leg 38 is constructed in one piece with septum 31. Leg 39 is constructed in one piece with septum 32. Bridge 40 is constructed in one piece with the bottom part 4 of the base element 3. The bearing element has the same thickness as septa 31 and 32. Legs 38 and 39 are constructed in a n acute taper. The measurements of bridge 40 have been chosen so that a small gap 37 remains between the tip of a septum 33 that is located between septa 31 and 32 and is associated with base element 2. Gap 37 ensures that the septum 33 does not rest against bridge 40, which could result in damage.

During operation, the bioreactor according to the invention is positioned so that the longitudinal side parts 6 of base elements 2 and 3 are vertically positioned. Accordingly, the length of longitudinal side parts 6 corresponds to the height of the bioreactor, which may be, for example, approximately 2 meters. The length of transverse side parts 7 of base elements 2 and 3 defines the width of the bioreactor, which may be, for example, approximately 1 meter. The depth of the bioreactor may be, for example, 1.5 to 5 cm.

The invention claimed is:

1. Bioreactor for air-lift culture of microorganisms, comprising
 a housing having longitudinal side walls vertically disposed and a gas inlet disposed such that the gas rises toward the top of the housing;
 the housing consisting of a first and a second one-piece trough-like base elements of light-permeable material, wherein each of the first and second base element comprises a bottom part, parallel longitudinal side walls and parallel transverse side walls, and wherein the first and second base element are connected to each other and face each other to enclose an inner volume with an inside depth T; and
 a flow guide for the air-lift flow, constructed in one piece with a base element, comprising equally spaced transversal septa which alternately protrude from the bottom part of the first and second base elements and which are arranged crosswise to the air-lift flow, perpendicular to the longitudinal side walls and parallel to the transverse side walls, wherein the septa have an inside depth $T_2$ which is smaller than the inside depth T of the bioreactor and having gaps between the end of each septum of the first base element and the bottom part of the opposing second base element and vice-versa, such that the flow cross-section is substantially decreased by said gaps and throttling points are created.

2. The bioreactor according to claim 1, wherein said base elements comprise light-permeable plastic foil.

3. Bioreactor according to claim 1, characterized in that the septa are arranged inside the housing in such a way that an essentially meander-shaped flow path for gas bubbles between the septa inside the housing and fluid between the septa will move in a revolving shape.

4. The bioreactor of claim 3, wherein said base elements are deep-drawn foil.

5. Bioreactor according to claim 1, characterized in that the septa are arranged in the housing in such a way that they limit the flow cross-section in each case to only a gap, whereby the gaps defined by the septa are arranged so as to alternate on opposing side walls of the housing.

6. Bioreactor according to claim 1, characterized in that the septa are interconnected by at least one support element.

7. Bioreactor according to claim 1, characterized in that the first and second base elements are identical and are arranged on each other so as to exactly cover each other.

8. Bioreactor according to claim 6, characterized in that the flow guide comprises at least one septum through which two side parts, called longitudinal side parts, which are arranged parallel, opposite from each other at a right angle to the septum, are interconnected in such a way that in the trough-like base element several chambers that are open on the side facing away from the associated bottom part are formed, whereby the at least one septum has a septum depth ($T_2$) that is smaller than or equal to the inside depth (T) of the reactor and greater than half of the inside depth (T) of the reactor, whereby the distances (D) between the individual septa are equal and the distance ($D_1$) between a side part called the first transverse side part and a consecutive septum do not equal the distance ($D_2$) between a side part called the second transverse side part and a consecutive septum or an integer multiple of it, whereby the identically constructed base elements with their chamber openings are arranged opposite each other in such a way on top of each other that the distance ($D_2$) overlaps the first distance ($D_1$).

9. Bioreactor according to claim 7, characterized in that the light-permeable material of the base elements a comprises flexible foil.

10. Bioreactor according to claim 8, characterized in that at least one of the base elements is provided in longitudinal direction with at least one reinforcement.

11. Bioreactor according to claim 10, characterized in that the reinforcement is formed by several U-shaped bearing elements, which are individually connected with two adjoining septa and in between with the bottom part of the associated base element, whereby the first and second transverse side part each are also connected via a U-shaped bearing element with the following septum.

12. Bioreactor according to claim 11, characterized in that the septa has a wall thickness which increases towards the bottom part of the associated base element.

13. Bioreactor according to claim 1, characterized in that both of the first and second base elements are provided on the edges of their side parts that are at a distance to the bottom part with a collar projecting essentially at a right angle outward.

14. Bioreactor according to claim 13, characterized in that the side parts of the base element have a wall thickness which is greater than the wall thickness of the septa of base element.

15. Bioreactor according to claim 14, characterized in that the two base elements are glued to each other or welded to each other via ultrasound at the respective outward-projecting collar of the edge, located at a distance from the bottom part, of the side parts of the base element.

16. Bioreactor according to claim 1, characterized in that the reactor space formed by both of the first and second base elements has a surface enlargement greater than a straight-surfaced enveloping surface of its volume.

17. Bioreactor according to claim 1, characterized in that it has devices for a turbulent flow configuration.

18. Bioreactor according to claim 1, characterized in that it has elements that guide the light from outside into the reactor space.

19. Bioreactor according to claim 1, characterized in that it has connections and connecting lines for supplying and/or removing gases and/or fluids.

20. Bioreactor according to claim 19, characterized in that the connecting lines can be cooled and/or heated.

21. Bioreactor according to claim 1, characterized in that it is part of a system of several individual bioreactors that are arranged serially on the fluid side.

22. Method for producing a bioreactor according to claim 1, wherein in a first step a strand from a light-permeable material is produced, said strand comprising a plurality of directly adjoining, serially arranged base elements according to claim 1, whereby the base elements are arranged behind each other in each case in orientation ($D_2$) of one base element followed by ($D_1$) of another base element, wherein, in a second step, the strand is divided into the individual base elements, and wherein, in a third step, two each consecutive base elements are arranged on top of each other by folding over a second base element onto a first base element in the manner described in claim 1.

23. A method for producing a bioreactor in accordance with claim 18, wherein the two base elements are glued to each other or welded to each other via ultrasound at the respective projecting collar of the edge, located at a distance from the bottom part, of the side parts of the base element.

24. Method for producing a bioreactor in accordance with claim 18, wherein the strand is produced by injection molding.

25. Method for cultivating microorganisms, wherein these are introduced into a bioreactor according to claim 1 that has been filled with a fluid and are cultivated therein.

26. Method according to claim 25, wherein the cultivation is performed with introduction of gas.

27. Method according to claim 25, wherein the cultivation is performed with addition of $CO_2$.

28. Method according to claim 25, wherein the cultivation takes place with cooling.

\* \* \* \* \*